US005948411A

United States Patent [19]

Koyama et al.

[11] Patent Number: 5,948,411

[45] Date of Patent: Sep. 7, 1999

[54] STABILIZED LIVE VACCINE

[75] Inventors: Kuniaki Koyama; Juichiro Osame, both of Mitoyo-gun, Japan

[73] Assignee: The Research Foundation for Microbial Diseases of Osaka University, Osaka, Japan

[21] Appl. No.: 08/322,036

[22] Filed: Oct. 12, 1994

Related U.S. Application Data

[63] Continuation of application No. 07/929,374, Aug. 14, 1992, abandoned.

[30] Foreign Application Priority Data

| | | | |
|---|---|---|---|
| May 5, 1992 | [JP] | Japan | 4-157236 |
| May 15, 1992 | [JP] | Japan | 4-148476 |

[51] Int. Cl.[6] ..... A61K 39/165; A61K 39/12; C12N 7/00; C12N 7/04

[52] U.S. Cl. ..... 424/212.1; 424/218.1; 424/230.1; 424/204.1; 424/202.1; 424/456; 424/461; 435/235.1; 435/236

[58] Field of Search ..... 424/202.1, 230.1, 424/212.1, 218.1, 456, 461, 204.1; 435/235.1, 236

[56] References Cited

U.S. PATENT DOCUMENTS

| | | | |
|---|---|---|---|
| 3,915,794 | 10/1975 | Zygraich et al. | 195/1.8 |
| 4,000,256 | 12/1976 | Hilleman et al. | 424/89 |
| 4,337,242 | 6/1982 | Mankus et al. | 424/202.1 |
| 4,338,335 | 7/1982 | McAleer et al. | 424/361 |
| 4,452,734 | 6/1984 | Larson et al. | 530/395 |
| 4,464,474 | 8/1984 | Coursaget et al. | 436/513 |
| 4,500,512 | 2/1985 | Barme . | |
| 4,555,401 | 11/1985 | Arimura et al. | 424/89 |
| 4,849,358 | 7/1989 | Chazono et al. . | |
| 4,985,244 | 1/1991 | Makino et al. | 424/89 |

FOREIGN PATENT DOCUMENTS

| | | |
|---|---|---|
| 7492187 | 9/1980 | Australia . |
| 0028563 | 5/1981 | European Pat. Off. . |
| 0065905 | 12/1982 | European Pat. Off. . |
| 0252059 | 1/1988 | European Pat. Off. . |
| 3364 | 4/1961 | France . |

OTHER PUBLICATIONS

Bio Rad Life Science Research Products; Price List R Jan. 1992 p. 65.

Dawson et al Eds *Data For Biochemical Research* 3rd ed Clarendon Press, Oxford, 1987 pp. 404–405.

Wang, Yu–Chan John et al., Journal of Parenteral Science and Technology; 42(25):54–525, 1988.

Shiraki, Kimiyasu, et al. Journal of General Virology; 72, 1393–1399, 1991.

BioRad Life Science Research Products; Price List R Jan. 1992, p. 7.

"Fields Virology", Second Edition, vol. 1, p. 782 (1990).

S. Karger, "Developments in Biological Standardization", vol. 48, 207–234 (1981).

World Health Organization Technical Report Series, No. 725, pp. 102–133 (1985).

*Primary Examiner*—Lynette F. Smith
*Assistant Examiner*—Datquan Lee
*Attorney, Agent, or Firm*—Birch, Stewart, Kolasch & Birch, LLP

[57] ABSTRACT

Disclosed is a stabilized live vaccine containing a varicella virus and a stabilizer, wherein the vaccine is substantially free of $Ca^{2+}$ ions and $Mg^{2+}$ ions. This stabilized live vaccine is extremely excellent in storage stability and heat resistance. Also disclosed is an improved stabilizer for a live varicella vaccine, comprising at least one member selected from gelatin and hydrolyzed gelatin, each being substantially free of $Ca^{2+}$ ions and $Mg^{2+}$ ions. The stabilizer can advantageously be used to stabilize a live vaccine containing a varicella virus. The substantial freedom of $Ca^{2+}$ ions and $Mg^{2+}$ ions can be attained by masking $Ca^{2+}$ ions and $Mg^{2+}$ ions present in a live vaccine containing a varicella virus and a stabilizer, with a chelating reagent, or by using as a stabilizer gelatin and/or a gelatin derivative after being purified to remove $Ca^{2+}$ ions and/or $Mg^{2+}$ ions contained therein.

10 Claims, No Drawings

STABILIZED LIVE VACCINE

This application is a continuation of application Ser. No. 07/929,374 filed on Aug. 14, 1992, now abandoned.

BACKGROUND OF THE INVENTION

1. Field of the Invention

The present invention relates to a stabilized live vaccine having excellent storage stability and excellent heat resistance. More particularly, the present invention is concerned with a stabilized live varicella vaccine comprising a virus component comprised of a varicella virus, and a stabilizer, wherein the vaccine is substantially free of $Ca^{2+}$ ions and $Mg^{2+}$ ions. The present invention is further concerned with a stabilizer comprising at least one member selected from gelatin and a gelatin derivative, each being substantially free of $Ca^{2+}$ ions and $Mg^{2+}$ ions, which stabilizer is useful for the stabilization of a live vaccine comprising a varicella virus as a virus component.

2. Discussion of Related Art

Since 1974, when WHO (the World Health Organization) started the worldwide Expanded Programme on Immunization (EPI), the demand for various vaccines which are excellent in both storage stability and heat resistance has been increasing. In order to meet the demand, research for developing vaccines having more improved stability has been extensively made in many parts of the world. As a result of the research, some types of vaccines which can be used at ambient temperatures in any of the tropics and the cold districts of the world, have been developed and put to practical use. Examples of these known improved vaccines include pertussis toxoid, and a trivalent DPT (diphtheria-pertussis-tetanus) vaccine using the above toxoid (U.S. Pat. No. 4,849,358), and lyophilized inactivated Japanese encephalitis vaccine [Fields "Virology", Second Edition, volume 1, p.782–783, published by Raven Press (New York, U.S.A.) in 1990].

However, there are various types of vaccines which have not yet been satisfactorily improved in stability. For example, with respect to live virus vaccines, such as those of measles, rubella, mumps and varicella, improvement in heat stability has been attained to some extent by lyophilization, but the improvement is still unsatisfactory. Especially, varicella virus for use in a live vaccine has extremely low thermal stability, so that it is usually necessary to preserve the virus at a temperature of −60° C. or lower. In general, viruses belonging to the herpesvirus family, which are susceptive to cell association, e.g., varicella virus, are extremely poor in heat stability. Due to this instability to heat, it has been very difficult to develop a satisfactory stabilizer for varicella virus vaccine. Thus, with respect to not only a live varicella virus vaccine but also a mixed live vaccine comprising varicella virus and other viruses, such as viruses of measles, rubella and mumps, it has been very difficult to realize varicella virus-containing live virus vaccines having excellent heat resistance.

In general, as materials which are usually used as stabilizers for vaccines, there can be mentioned, for example, amino acids, such as sodium glutamate, arginine, lysine, and cysteine; monosaccharides, such as glucose, galactose, fructose, and mannose; disaccharides, such as sucrose, maltose, and lactose; sugar alcohols such as sorbitol and mannitol; polysaccharides, such as oligosaccharide, starch, cellulose, and derivatives thereof; human serum albumin and bovine serum albumin; gelatin, and gelatin derivatives, such as hydrolyzed gelatin; and ascorbic acid as an antioxidant. These materials are described in publications, e.g., "Toketsu-Kanso To Hogo Busshitsu (Lyophilization And Protective Materials)" written by Nei, p. 1–176, published by Tokyo Daigaku Shuppan Kai (Publishing Association of the University of Tokyo), Japan in 1972; and "Shinku Gijutsu Koza (8): Sinku Kanso (Lecture on Vacuum Technology (8): Vacuum Drying)" written by Ota et al., p.176–182, published by Nikkan Kogyo Shimbun Co., Ltd., Japan in 1964.

However, the stabilizing effects of these materials are generally poor when they are used individually. Therefore, these stabilizers are usually employed in combination. For example, a 4-component mixed stabilizer has been proposed, in which four types of components, respectively selected from amino acids, saccharides, sugar alcohols and peptones, are used in combination, so that the stabilizing effect can be synergistically or additively increased.

As mentioned above, a live varicella vaccine is extremely poor in heat stability. Even if amino acids, saccharides, sugar alcohols, gelatin and gelatin derivatives, which are widely used as stabilizers in other types of live virus vaccines, are added to a live varicella vaccine, satisfactory stability of a live varicella vaccine cannot be attained. Therefore, when a live varicella vaccine containing these conventional stabilizers added thereto is preserved at room temperature for a long period of time, the infectivity titer of the vaccine is likely to be lowered. That is, not only in the case of a live varicella vaccine comprising a varicella virus as a single virus component, but also in the case of a mixed (multivalent) live vaccine comprising a varicella virus and other viruses, such as live viruses of measles, rubella, mumps, poliomyelitis and influenza, a satisfactory stability cannot be attained even when conventional stabilizers, which are effective for stabilizing a live virus vaccine other than a live varicella vaccine, are added. Therefore, it has been very difficult to provide a stable live vaccine containing a varicella virus.

Further, conventionally, when gelatin and/or a gelatin derivative, such as hydrolyzed gelatin, which are effective for stabilizing live vaccines of measles, rubella and mumps, are added to a live vaccine containing varicella virus, a problem that the stability of the vaccine is even lowered, has been experienced. Even when only stabilizers other than gelatin and/or a gelatin derivative such as hydrolyzed gelatin are used, serious problems have frequently been encountered in connection with mixed vaccines containing a live varicella virus. Illustratively stated, when a live vaccine is prepared by the use of a virus other than varicella virus, e.g., measles virus harvested from a culture system thereof, the stability of the vaccine is maintained by simply adding conventional stabilizers other than gelatin and a gelatin derivative. Nevertheless, when live varicella virus harvested from a culture system thereof is added to the above vaccine, the resultant mixed vaccine is likely to be lowered in the stability of the varicella virus, so that the mixed vaccine cannot exhibit a satisfactory function as a mixed vaccine containing live varicella virus.

SUMMARY OF THE INVENTION

In these situations, the present inventors have made extensive and intensive studies to solve the above-mentioned difficult problems in order to provide a stabilized live vaccine comprising, as a virus component, an attenuated live varicella virus. As a result, they have unexpectedly found that when a chelating reagent, such as ethylenediaminetetraacetic acid (EDTA), is added to a live varicella vaccine which has conventionally been poor in stability irrespective of the presence or absence of gelatin and/or a gelatin derivative such as hydrolyzed gelatin (which have been conventionally regarded as being useful for stabilizing other types of live virus vaccines), the stability of the varicella virus-containing vaccine is greatly improved. The present inventors have further studied the reason why the improved stability can be attained by the addition of EDTA. As a result, they have unexpectedly found that the stability of a live varicella virus vaccine depends upon the presence or absence of $Ca^{2+}$ ions and $Mg^{2+}$ ions and that the essential requirement for the stabilization of a live varicella virus vaccine is to render the varicella vaccine substantially free of $Ca^{2+}$ and $Mg^{2+}$. This is very surprising in view of the fact that the stability of various live vaccines, e.g., poliovirus vaccine, is rather improved by the presence of $Ca^{2+}$ ions and $Mg^{2+}$ ions.

In many cases, $Ca^{2+}$ ions and $Mg^{2+}$ ions are introduced when a cell culture is prepared for the multiplication of a virus. Also it is known that gelatin, which is widely used in recent years as a representative stabilizer component for various vaccines, contains about 0.1% or less of $Ca^{2+}$ ions and that commercially available hydrolyzed gelatin contains about 0.1% $Ca^{2+}$ ions and about 0.01% $Mg^{2+}$ ions.

The exact mechanism in which such $Ca^{2+}$ ions and $Mg^{2+}$ ions impair the stability of a live vaccine containing varicella virus has not yet been elucidated. It is presumed, however, that the inactivation of live varicella virus by heat would disadvantageously be promoted by the action of these specific ions, thus lowering the infectivity titer of the vaccine and that the coagulation of the varicella virus particles would be induced by the action of these specific ions, thus causing the vaccine to become unstable.

EDTA has not been considered to be a favourable additive for use in a vaccine because EDTA has stinging properties. However, during the study by the present inventors, it has been unexpectedly found that by the addition of EDTA to a live vaccine containing a varicella virus and a stabilizer, the stability of the vaccine can be greatly enhanced. The reason for this is believed to reside in that EDTA acts as a chelating reagent on $Ca^{2+}$ ions and $Mg^{2+}$ ions derived from cultured cells and a stabilizer, to thereby mask the ions.

Based on the above-mentioned novel findings, the present invention has been completed.

It is, therefore, an object of the present invention to provide a live vaccine containing an attenuated varicella virus and a stabilizer, which has high stability.

It is another object of the present invention to provide a stabilized live vaccine having excellent stability, which comprises attenuated live varicella virus and, as a stabilizer, at least one member selected from the group consisting of gelatin and a gelatin derivative such as hydrolyzed gelatin, the stabilizers having been considered to be extremely effective for the stabilization of live vaccines other than a live varicella virus vaccine, but considered to have no effect for the stabilization of a live varicella vaccine but rather have an adverse effect therefor.

It is a further object of the present invention to provide a stabilizer for a live vaccine comprising a varicella virus, which comprises at least one member selected from the group consisting of a treated gelatin and a treated gelatin derivative which are respectively obtained by subjecting commercially available gelatin and a commercially available gelatin derivative such as hydrolyzed gelatin (the gelatin and gelatin derivative having not been actually utilized as a stabilizer for a live vaccine containing varicella virus), to a treatment for masking or removing $Ca^{2+}$ ions and $Mg^{2+}$ ions contained therein.

The foregoing and other objects, features and advantages of the present invention will be apparent from the following detailed description and appended claims.

DETAILED DESCRIPTION OF THE INVENTION

Essentially, according to the present invention, there is provided a stabilized live vaccine comprising a virus component comprised of at least one varicella virus selected from the group consisting of an attenuated live varicella virus and an attenuated recombinant varicella virus, and a stabilizer, wherein the vaccine is substantially free of $Ca^{2+}$ ions and $Mg^{2+}$ ions.

The attenuated live varicella virus in the present invention comprises at least one varicella virus selected from the group consisting of an attenuated live varicella virus and an attenuated live recombinant varicella virus, which can be prepared by conventional methods. The Oka Strain (U.S. Pat. No. 3,985,615; Virus Deposit No. ATCC VR-795) is well known as an attenuated live varicella virus strain which is especially useful for producing a live varicella vaccine. An attenuated live recombinant varicella virus can be produced by the recombination of the genomic DNA of the Oka strain with a foreign gene. The recombination can be easily conducted by conventional methods. With respect to the details of a recombination method in which a virus gene is recombined with a foreign gene, reference may be made to European Patent Application Publication No. 0 334 530 A1. This virus strain (Oka strain) can be advantageously used in the present invention, but the varicella virus in the present invention is never limited to this strain.

It is required that the live vaccine of the present invention be substantially free of $Ca^{2+}$ ions and $Mg^{2+}$ ions. The terminology "substantially free of $Ca^{2+}$ ions and $Mg^{2+}$ ions" used herein means that $Ca^{2+}$ ions and $Mg^{2+}$ ions are substantially not detected by the calorimetric titration method using a chelating reagent.

When $Ca^{2+}$ ions and $Mg^{2+}$ ions derived from cultured cells are contained in a vaccine, these ions can be masked by adding a chelating reagent to form a chelate compound with the ions.

As chelating reagents, there can be employed water-soluble materials capable of forming a chelate compound. Examples of water-soluble chelating reagents capable of forming a chelate compound include polyaminocarboxylic acids, such as ethylenediaminetetraacetic acid (hereinafter referred to as "EDTA"), and a salt thereof; oxycarboxylic acids, such as citric acid, and a salt thereof; and condensed phosphates, such as ultraphosphate.

Particularly with respect to EDTA, there are various commercially available products of EDTA and salts thereof, including salts thereof with Ca, Co, K, Na, Li, Ni, Ba, Bi, Mg, Mn, La, and ammonium. Of these, the Ca salt and Mg salt are not preferred. Preferred salts are the Na salt and K salt. In addition, from the viewpoint of minimizing the variation of pH due to the addition of EDTA, it is also preferred to use the disodium salt of EDTA or the trisodium salt of EDTA. Further, water-soluble ethyleneglycol tetraacetic acid and a salt thereof, which are analogs to EDTA, can be used as a chelating reagent in the present invention.

As stabilizers to be used in the present invention, there can be mentioned conventionally known stabilizers, such as sucrose, lactose, sorbitol, sodium glutamate, cysteine, gelatin, and a gelatin derivative such as hydrolyzed gelatin.

At least one member selected from the group consisting of gelatin and a gelatin derivative is particularly useful as a stabilizer component.

In the present invention, gelatin and a gelatin derivative can be used individually or in combination.

As gelatin, there can be mentioned, for example, a purified gelatin described in the Japanese Pharmacopeia.

Examples of gelatin derivatives include hydrolyzed gelatin and chemical derivatives thereof. The terminology "hydrolyzed gelatin" means either a hydrolyzed polypeptide obtained by subjecting gelatin to degradation through hydrolytic cleavage or a polypeptide obtained by polymerizing the above-mentioned hydrolyzed polypeptides. Hydrolyzed gelatin is water-soluble and has a molecular weight of about 35,000 or less.

As illustrative examples of gelatin derivatives usable in the present invention, there can be mentioned commercially available products, such as Gelysate (tradename of hydrolyzed gelatin manufactured and sold by BBL Co., Ltd., USA), and Physiogel, Neoplasmagel, Gelifundol and Haemaccel (tradenames of hydrolyzed gelatin or chemical derivative thereof manufactured and sold by Hoechst AG, Germany). Details of these gelatin derivatives are described in "Developments in Biological Standardization", Vol. 48, pp. 207–234, Karger (1981). In the present invention, the hydrolyzed gelatin which is easily available under the tradename Gelysate is preferably used.

The preferred amounts of gelatin and a gelatin derivative are, respectively, from about 0.02 to about 1.0% (w/v) and from about 0.5 to about 10% (w/v), in terms of the concentration in the stabilized live vaccine.

Commercially available gelatin and gelatin derivatives, particularly hydrolyzed gelatin usually contain $Ca^{2+}$ ions and/or $Mg^{2+}$ ions. Therefore, when these commercially available gelatin and gelatin derivative are used as they are, it is preferred to add a chelating reagent, such as the above-mentioned EDTA or a salt thereof, to the live vaccine.

The amount of a chelating reagent to be used in the present invention is not critical, as long as the amount is not smaller than an amount necessary for converting the $Ca^{2+}$ ions and $Mg^{2+}$ ions present in the vaccine into a chelate compound, to thereby mask these ions. The amount of a chelating reagent is usually from about 0.001 to about 0.1% (w/v) in terms of the concentration in the stabilized live vaccine.

As a solution for suspending a virus antigen, use can be made of 0.005 to 0.01M PBS (−) prepared in accordance with the method used in Reference Example 4 described later.

Also, Medium 199 (see Reference Example 10) and MEM (Minimum Essential Medium) (see Reference Example 1) which have been prepared without adding Ca and Mg compounds thereto can be used as a solution for suspending a virus antigen.

With respect to the concentration of each stabilizer component in a stabilized live vaccine, there may be mentioned, for example, from about 0.01 to about 5.0% (w/v) of sodium glutamate, from about 0.02 to about 1.0% (w/v) of cysteine, from about 0.5 to about 10% (w/v) of sucrose, from about 0.5 to about 10% (w/v) of lactose, from about 0.2 to about 6.0% (w/v) of sorbitol, from about 0.02 to about 1.0% (w/v) of gelatin, from about 0.5 to about 10% (w/v) of gelatin derivative such as hydrolyzed gelatin, and from about 0.001 to about 0.1% (w/v) of a chelating reagent such as EDTA or a salt thereof, in terms of the concentration in a stabilized live vaccine.

The final pH after the addition of a stabilizer is preferably 6.5 to 7.5. From the viewpoint of alleviating the pain and the occurrence of lesion upon administration of the vaccine by injection, it is preferred that the vaccine have its osmotic pressure around the isotonic point.

Following are four preferred examples of formulations of stabilizers useful for obtaining stabilized live vaccines of the present invention:

(1) a stabilizer comprising from about 0.01 to about 5% (w/v) of sodium glutamate, from about 0.5 to about 10% (w/v) of sucrose, from about 0.02 to about 1% (w/v) of gelatin and from about 0.5 to about 10% (w/v) of hydrolyzed gelatin, in terms of the concentration in the stabilized live vaccine;

(2) a stabilizer comprising from about 0.01 to 5% (w/v) of sodium glutamate, from about 0.5 to about 10% (w/v) of sucrose, from about 0.02 to about 1% (w/v) of gelatin, from about 0.5 to about 10% (w/v) of hydrolyzed gelatin and from about 0.001 to about 0.1% (w/v) of a chelating reagent, in terms of the concentration in the stabilized live vaccine;

(3) a stabilizer comprising from about 0.5 to about 10% (w/v) of lactose, from about 0.2 to about 6.0% (w/v) of sorbitol, from about 0.02 to about 1.0% (w/v) of cysteine, from about 0.01 to about 5.0% (w/v) of sodium glutamate, from about 0.02 to about 1.0% (w/v) of gelatin and from about 0.5 to about 10% (w/v) of hydrolyzed gelatin, in terms of the concentration in the stabilized live vaccine; and (4) a stabilizer comprising from about 0.5 to about 10% (w/v) of lactose, from about 0.2 to about 6.0% (w/v) of sorbitol, from about 0.02 to about 1.0% (w/v) of cysteine, from about 0.01 to about 5.0% (w/v) of sodium glutamate, from about 0.02 to about 1.0% (w/v) of gelatin, from about 0.5 to about 10% (w/v) of hydrolyzed gelatin and from about 0.001 to about 0.1% (w/v) of a chelating reagent, in terms of the concentration in the stabilized live vaccine.

Hereinbelow, the illustrative procedure to practice the present invention will be explained.

(1) Preparation of a virus suspension which is substantially free of $Ca^{2+}$ ions and $Mg^{2+}$ ions:

With respect to a varicella virus, for example, varicella virus is cultured using a host cell and after completion of the culturing, the cultured medium is discarded from a culturing vessel. Then, a 0.01 M phosphate-buffered saline (PBS)(−) containing a trisodium salt of EDTA in a final concentration of 0.05% (w/v), is added and then, infected cells are detached from the inner wall surface of the culturing vessel. Then, low-speed centrifugation is performed to thereby collect the infected cells. A solution for suspending varicella virus, which contains the above-mentioned stabilizer dissolved therein, is added to the collected infected cells to thereby suspend the infected cells. Subsequently, the infected cells are disrupted by means of a homogenizer or by ultrasonication and then, the cell debris are removed, to thereby prepare a virus suspension.

With respect to other viruses, for example, viruses of measles, rubella and mumps, a virus suspension can be prepared by a method in which during the culturing or after completion of the culturing, the cultured medium containing $Ca^{2+}$ ions and $Mg^{2+}$ ions is replaced by Medium 199 or MEM which has been prepared without adding Ca and Mg compounds.

For example, with respect to a measles virus, a virus suspension can be prepared by washing the infected cells with the PBS(−) prepared in Reference Example 4 described later, to remove $Ca^{2+}$ ions and $Mg^{2+}$ ions; suspending the infected cells in Medium 199 or MEM each free of both $Ca^{2+}$ ions and $Mg^{2+}$ ions; and freeze-thawing the resultant suspension, followed by low-speed centrifugation to collect a supernatant as a virus suspension.

With respect to respective viruses of rubella and mumps, a virus suspension can be prepared, for example, by concentrating the cultured medium containing the virus by means of, for example, a fractionating membrane; subjecting the resultant concentrated medium to ultracentrifugation to collect the virus; and suspending the virus in Medium 199 or MEM each free of both $Ca^{2+}$ ions and $Mg^{2+}$ ions.

A stabilizer can be added to the thus obtained virus suspension.

(2) Preparation of a virus suspension in which $Ca^{2+}$ ions and $Mg^{2+}$ ions derived from cultured cells have been converted into a chelate compound to mask the ions:

For example, a chelating reagent can be added to a virus suspension to thereby convert these metal ions into a chelate compound and mask the ions.

(3) Preparation of gelatin and hydrolyzed gelatin in which $Ca^{2+}$ ions and $Mg^{2+}$ ions have been converted into a chelate compound to mask the ions:

For example, a chelating reagent is added to a gelatin solution or a hydrolyzed gelatin solution, to thereby convert these metal ions into a chelate compound and mask the ions. Such chelating reagent-treated gelatin and chelating reagent-treated hydrolyzed gelatin are very useful as a stabilizer for a live varicella vaccine.

(4) Preparation of purified gelatin and purified hydrolyzed gelatin which are substantially free of $Ca^{2+}$ ions and $Mg^{2+}$ ions:

Purification can be conducted by a conventional method using, for example, at least one treatment selected from the group consisting of dialysis treatment, gel filtration treatment, cation exchange resin treatment and chelating resin treatment. For example, by subjecting the above-mentioned gelatin and hydrolyzed gelatin, in which the above-mentioned metal ions are masked or not masked by a chelating reagent, to gel filtration treatment or by subjecting a solution of the gelatin and a solution of the hydrolyzed gelatin to dialysis treatment, a purified gelatin and a purified hydrolyzed gelatin, which are substantially free of the above-mentioned metal ions, can be obtained. The thus obtained purified gelatin and purified hydrolyzed gelatin are very useful as a stabilizer for a live varicella vaccine.

(5) Preparation of a stabilized live varicella vaccine:

Varicella virus is cultured by the use of a human diploid cell, and the obtained culture is purified, for example, by centrifugation, to thereby obtain a varicella virus fraction. To the obtained virus fraction is added a vaccine stabilizer, and the resultant mixture is diluted so that the virus content per dose of a stabilized live vaccine becomes 1,000 PFU (plaque-forming unit) or more, to thereby obtain a stabilized live varicella vaccine. Aliquots of the thus prepared live vaccine are subjected to testings for safety, effectiveness and homogeneity, to thereby confirm the eligibility as a vaccine. These testings can be conducted in accordance with the Minimum Requirements for Biological Products (1989) provided for in the Notification No. 195 of the Ministry of Health and Welfare, Japan (see, for example, "Lyophilized Attenuated Live Varicella Vaccine" in the Minimum Requirements for Biological Products).

After the eligibility is confirmed, the vaccine is employed. A lyophilized vaccine can be prepared by lyophilizing the vaccine in a vial or an ampoule having a volume of about 3 to 30 ml, and is fluid-tightly sealed and stored at a temperature of 5° C. or less. The thus prepared vaccine is used in accordance with the instructions attached thereto. Illustratively stated, a lyophilized vaccine is completely reconstituted by means of sterile distilled water just before use, and the resultant solution is inoculated by hypodermic injection in an amount, for example, of 0.5 ml per dose.

As mentioned above, viruses of measles, rubella, mumps and the like are relatively, thermally stable, as compared with varicella virus. The stabilizers for vaccines of these viruses of measles, rubella and mumps resemble each other in formulation and it is known that saccharides, amino acids, sugar alcohols, gelatin and gelatin derivatives, are effective for the stabilization of these virus vaccines. However, these conventional stabilizers cannot be effectively used for a live vaccine containing varicella virus and/or a recombinant varicella virus.

By contrast, the stabilizer of the present invention is effective not only for a varicella vaccine containing varicella virus and/or a recombinant varicella virus alone, but also for a mixed (polyvalent) vaccine containing varicella virus and/or a recombinant varicella virus, and at least one virus other than varicella virus, such as viruses of measles, rubella, mumps, influenza, Japanese encephalitis and hepatitis. Examples of these mixed vaccines include a tetravalent live vaccine containing viruses of varicella, measles, rubella and mumps (see Japanese Patent Application Publication Specification No. 58-5169).

According to the present invention, there can be provided various types of stabilized vaccines, such as a lyophilized vaccine, a lyophilized mixed vaccine, a liquid vaccine and a liquid mixed vaccine, which are extremely excellent in storability and heat stability.

In the case of the preparation of a mixed live vaccine, respective bulk materials of live vaccines are diluted and mixed so that the content of each virus per dose of a live vaccine becomes 1,000 to 5,000 PFU or more, or 5,000 $TCID_{50}$ (median tissue culture infective dose) or more, to thereby obtain a final product of mixed live vaccine.

As described above, the stabilized live varicella vaccine of the present invention which comprises a virus component comprised of attenuated varicella virus and/or attenuated recombinant varicella virus, and a stabilizer, and which is substantially free of $Ca^{2+}$ ions and $Mg^{2+}$ ions, has excellent storage stability and excellent heat resistance.

The stabilized live vaccine may further comprise at least one attenuated live virus other than the varicella virus, such as viruses of measles, rubella, mumps, Japanese encephalitis, influenza and hepatitis E.

The stabilizer of the present invention which comprises gelatin and/or a gelatin derivative such as hydrolyzed gelatin, each being substantially free of $Ca^{2+}$ ions and $Mg^{2+}$ ions, is extremely useful for stabilizing a live vaccine comprising varicella virus and/or recombinant varicella virus as a virus component.

The present invention greatly contributes to the spread of vaccination on the global scale in line with the Expanded Programme on Immunization of WHO, and to the reduction of the cost of vaccination. Thus, the present invention contributes to the prevention of epidemics and the promotion of the health and hygiene of human beings.

PREFERRED EMBODIMENT OF THE INVENTION

The present invention will now be further illustrated in more detail with reference to the following Reference Examples and Examples which should not be construed to be limiting the scope of the present invention.

REFERENCE EXAMPLE 1

Culturing of Human Diploid Fibroblast MRC-5

Human diploid fibroblast MRC-5 is cultured at 37° C. using MEM (manufactured and sold by GIBCO, USA) for both growth and maintenance of the cells. Just before the medium is used, an aqueous 7% (w/v) $NaHCO_3$ solution is added to the medium for adjustment of pH. For the use as a growth medium, pH is adjusted to 7.0, and for the use as a maintenance medium, pH is adjusted to 7.5. Further, the medium is supplemented with commercially available fetal calf serum so that the final concentration of the serum becomes 10% (w/v) for the use as a growth medium and 3% (w/v) for the use as a maintenance medium.

REFERENCE EXAMPLE 2

Culturing of Varicella Virus

A seed virus of varicella virus Oka strain (WHO Technical Report Series, No. 275, pp. 102–124, 1985: ATCC VR-795) is inoculated into the MRC-5 cell culture obtained in Reference Example 1, at an MOI (multiplicity of infection) of 0.03, followed by culturing at 37° C. for 2 days. The maintenance medium described in Reference Example 1 is used as a medium for this culturing. During the culturing of the virus, the region of the infected cells gradually expands in accordance with the propagation of virus. When observation is made through a microscope, the virus-infected cells are found to exhibit rounding. Thus, the infected cells can be detected as the so-called CPE (cytopathogenic effect). Therefore, by making a microscopic observation of the expansion of the infected cells exhibiting the CPE, the degree of virus growth can be determined. At the time when the CPE is observed throughout the entire region of the cell culture monosheet, the virus culturing is terminated. A Roux bottle having a culturing area of 210 $cm^2$ is used as a culturing vessel.

REFERENCE EXAMPLE 3

Culturing of Viruses of Measles, Mumps and Rubella

In substantially the same manner as described in Reference Examples 1 and 2, chick embryo cells and quail embryo cells are individually cultured by the use of MEM, and each of measles virus and mumps virus is cultured in the resultant chick embryo cells, and rubella virus is cultured in the resultant quail embryo cells.

REFERENCE EXAMPLE 4

Preparation of M/100 PBS (−) [a Phosphate-Buffered Saline Free of $Ca^{2+}$ Ions and $Mg^{2+}$ Ions]

8.0 g of NaCl, 0.2 g of KCl, 2.9 g of $Na_2HPO_4.12H_2O$ and 0.2 g of $KH_2PO_4$ are dissolved in distilled water so that the total volume of the resultant PBS (−) becomes 1,000 ml. The pH of the obtained PBS (−) is about 7.4.

REFERENCE EXAMPLE 5

Preparation of a Liquid (A) for Suspending Virus 50 g of sucrose, 1.0 g of sodium L-glutamate and 0.1 g of trisodium salt of EDTA are added, in this order, to 800 ml of the PBS (−) obtained in Reference Example 4, to obtain a solution. Separately, 50 ml of distilled water is added to 2.0 g of gelatin, and 100 ml of distilled water is added to 25 g of hydrolyzed gelatin (manufactured and sold by BBL Co., Ltd., USA), and each of the resultant mixtures is individually heated in an autoclave to thereby obtain a solution. All of the solutions obtained above are mixed together, and distilled water is added thereto to make the total volume 1,000 ml. Subsequently, the resultant mixture is subjected to filtration sterilization, followed by subjecting an aliquot of the mixture to testing for sterility to confirm that the mixture is sterile. The composition of one liter of liquid (A) for suspending virus is shown in the following Table 1.

TABLE 1

| | |
|---|---|
| NaCl | 6.4 g |
| KCl | 0.16 g |
| $Na_2HPO_4.12H_2O$ | 2.3 g |
| $KH_2PO_4$ | 0.16 g |
| Sucrose | 50.0 g |
| Sodium L-glutamate | 1.0 g |
| Gelatin | 2.0 g |
| *Hydrolyzed gelatin | 25.0 g |
| *Trisodium salt of EDTA | 0.1 g |

<Note>
Components indicated by mark * are referred to in Reference Example 8.

REFERENCE EXAMPLE 6

Preparation of a Liquid (B) for Suspending Virus

In substantially the same manner as described in Reference Example 5, a liquid (B) for suspending virus is prepared using the components indicated in the following Table 2. Illustratively stated, gelatin and hydrolyzed gelatin are dissolved in distilled water to thereby obtain a solution. The other components are dissolved in 800 ml of PBS (−), to thereby obtain a solution. Then, these solutions are mixed together, and distilled water is added thereto so that the total volume of the resultant mixture becomes 1,000 ml. Subsequently, the mixture is subjected to filtration sterilization. The sterilized filtrate is employed as liquid (B) for suspending virus.

TABLE 2

| | |
|---|---|
| NaCl | 6.4 g |
| KCl | 0.16 g |
| $Na_2HPO_4.12H_2O$ | 2.3 g |
| $KH_2PO_4$ | 0.16 g |
| Lactose | 50.0 g |
| D-Sorbitol | 20.0 g |
| L-cysteine | 2.0 g |
| Sodium L-glutamate | 1.0 g |
| Gelatin | 7.5 g |
| Hydrolyzed gelatin | 25.0 g |
| Trisodium salt of EDTA | 0.1 g |

REFERENCE EXAMPLE 7

Preparation of a Liquid (C) for Suspending Virus

In substantially the same manner as described in Reference Example 6, a solution having a twofold concentration of each component of liquid (B) for suspending virus is prepared. The prepared solution is employed as liquid (C) for suspending virus.

REFERENCE EXAMPLE 8

Preparation of Liquids 1 to 8

Substantially the same procedure as described in Reference Example 5 is repeated except that the concentrations (g/liter) of hydrolyzed gelatin and trisodium salt of EDTA (both indicated by mark * in Reference Example 5) are varied as indicated in the following Table 3.

TABLE 3

| | Hydrolyzed gelatin (g/liter) | Trisodium salt of EDTA (g/liter) |
|---|---|---|
| Liquid 1 | 0 | 0 |
| Liquid 2 | 10 | 0 |
| Liquid 3 | 25 | 0 |
| Liquid 4 | 50 | 0 |
| Liquid 5 | 0 | 0.1 |
| Liquid 6 | 10 | 0.1 |
| Liquid 7 | 25 | 0.1 |
| Liquid 8 | 50 | 0.2 |

REFERENCE EXAMPLE 9

Preparation of Purified Hydrolyzed Gelatin Which is Free of $Ca^{2+}$ Ions and $Mg^{2+}$ Ions To 120 g of hydrolyzed gelatin (manufactured and sold by BBL Co., Ltd., USA) is added 180 ml of distilled water, and the resultant mixture is heated in an autoclave, to thereby dissolve the hydrolyed gelatin. Subsequently, distilled water is added thereto to make the total volume 300 ml, thereby obtaining a 40% (w/v) aqueous hydrolyzed gelatin solution.

The prepared hydrolyzed gelatin solution is poured into a dialysis tube made of cellulose ester, namely, Spectra/Por (fractionating molecular weight: 1,000; manufactured and sold by Funakoshi Pharmaceutical Co., Ltd., Japan), and dialyzed at room temperature for 48 hours, against distilled water employed as an external liquid. After completion of the dialysis, the obtained dialysate is subjected to chelatometric titration to confirm that $Ca^{2+}$ ions and $Mg^{2+}$ ions are not detected, indicating that these ions have been substantially eliminated. After the confirmation, the dialysate is then subjected to filtration sterilization. The resultant sterile filtrate is employed as purified hydrolyzed gelatin for use as a stabilizer component for a live vaccine.

The above chelatometric titration is performed by using disodium salt of EDTA as a chelating reagent, and by colorimetric titration using Eriochrome Black T as a metal indicator. In the colorimetric titration, when the color of the assay system has changed from purplish red to blue, the titration is terminated.

REFERENCE EXAMPLE 10

Plaque Assay of Varicella Virus

10-Fold serially diluted virus-containing liquids to be tested are individually inoculated into a monosheet of MRC-5 cells cultured in a Petri dish, followed by culturing at 37° C. in an incubator containing 5% (v/v) carbon dioxide. A maintenance medium is prepared in substantially the same manner as in Reference Example 1 except that Medium 199 (manufactured and sold by DIFCO, USA) is used as a basal medium. Agarose is added to the maintenance medium in a final concentration of 0.8% (w/v), to thereby prepare a solid medium. The thus prepared solid medium is overlaid upon a monosheet of the infected cells. Staining of the infected cultured cells is performed by a method in which a medium prepared by adding Neutral Red to the above-mentioned solid medium in a final concentration of 0.01% (w/v) is further overlaid upon the solid medium which is overlaid upon the infected cells. Then, the number of plaques having appeared is counted. The number of the plaques, i.e., PFU (plaque-forming unit), indicates the virus content of a live vaccine, and the titer of a live vaccine is indicated in terms of PFU. For instance, when the inoculation of 1 ml of a $10^4$-fold diluted vaccine, followed by culturing, produces 10 plaques, the total number of the plaques is estimated to be $10^5$ PFU/ml, which is calculated from $10\times10^4$, and the total number is usually indicated as 5.0, in accordance with the common logarithm of $10^5$.

REFERENCE EXAMPLE 11

Determination of Titer of a Live Vaccine of Each of Measles, Rubella and Mumps

With respect to the titers of measles vaccine and rubella vaccine, the plaque assay of measles virus is made using Vero cells and that of rubella virus is made using RK-13 cells, each in substantially the same manner as described in Reference Example 10, to thereby determine the titer.

With respect to a mumps vaccine, the titer thereof is assayed in terms of $TCID_{50}$ of mumps virus, using Vero cells. $TCID_{50}$ is determined as follows: 10-fold serially diluted vaccine solutions to be tested are individually inoculated into Vero cell sheets cultured in test tubes, each having a volume of 5 ml, followed by culturing at 37° C. $TCID_{50}$ is determined on the basis of the dilution multiple of the vaccine at which multiple the CPE is microscopically observed in 50% of the infected cells (see "Review of Medical Microbiology", 13th ed., pp. 344–345, Lange Medical Publications, 1976). For example, a $10^4$-fold diluted vaccine solution is inoculated into 10 test tubes each containing a cell sheet, and is cultured therein. In this case, when the CPE is observed in 5 (50%) of the 10 test tubes after the culturing, the $TCID_{50}$ is indicated as 4.0, in accordance with log $10^4$.

EXAMPLE 1

Storage Stability Testing of Live Vaccine (Effectiveness Testing of a Stabilizer)

Into MRC-5 cell cultures in 20 Roux bottles, each having a culturing area of 210 $cm^2$, is inoculated varicella virus Oka strain seed virus, followed by culturing in substantially the same manner as described in Reference Example 2. After completion of the culturing, the cultured medium is discarded. The infected cells in each Roux bottle are washed twice with 200 ml of PBS (–). Subsequently, 20 ml of 0.05% (w/v) trisodium salt of EDTA is superposed upon the infected cells in each Roux bottle, and the cells are detached, by pipetting, from the inner wall surface of the Roux bottle and suspended in the liquid, to thereby obtain an infected-cell suspension. The thus obtained infected-cell suspensions in the bottles are pooled together. Thus, a total of 400 ml of an infected-cell suspension is obtained. The obtained suspension is divided into 8 equivolume aliquots and placed in 8 centrifugal tubes (T1 to T8), to thereby prepare 8 centrifugal tubes each containing an infected-cell suspension in an amount of 50 ml. The infected-cell suspension in each centrifugal tube is centrifuged at 2,000 rpm for 10 minutes at 4° C. to thereby separate the suspension into a supernatant and the cells. The supernatant is discarded, so that pellets of the infected cells on the bottom of the centrifugal tube are obtained. Liquids 1 through 8 prepared in Reference Example 8 are placed in the centrifugal tubes in such a manner that the liquid numbers correspond to the tube numbers, i.e., a 20 ml aliquot of liquid 1 is placed in the centrifugal tube T1, a 20 ml aliquot of liquid 2 is placed in the centrifugal tube T2 and so on, to thereby re-suspend the infected cells. Then, the resultant suspension is subjected to one cycle of freeze-thawing. Subsequently, the suspension is subjected to ultrasonication (20 kHz, 150 mA, 0.3 second/ml) in an ice water bath, followed by centrifugation at 1,000 rpm for 10 minutes at 4° C., to thereby separate the suspension into the cells and a supernatant. The supernatant containing virus separated from the cells is collected to thereby prepare 8 types of live vaccines having different stabilizer compositions.

Each type of live vaccine is dispensed into vials each having a volume of 3 ml in an amount of 0.5 ml per vial, followed by lyophilization. Filling of the vial with nitrogen gas, and air-tight sealing of the vial with a rubber stopper are conducted. These vaccine vials are stored at 37° C. Every one week during the storing, 5 vials are arbitrarily picked up and subjected to testing for effectiveness of the stabilizer. Just before the test is performed, 0.7 ml of distilled water for injection is added to the lyophilized vaccine for reconstitution thereof to thereby obtain a solution containing the vaccine completely dissolved therein. The effectiveness testing is performed with respect to the obtained solution by the plaque assay described in Reference Example 10. The titer of each type of vaccine is indicated in terms of PFU. Results are summerized in Table 4 below. The stabilizing effect exhibited by Liquid 7 is most excellent.

TABLE 4

Storage Stability Test of Live Varicella Vaccine (Testing for effectiveness of Stabilizer)

| Stabilizer Liquid No. | Titer = log (PFU/ml) Before lyophilization | Days of storing at 37° C. after lyophilization 0 | 7 | 14 | 21 | 28 |
|---|---|---|---|---|---|---|
| 1 | 5.3 | 4.3 | 3.5 | 2.7 | 2.5 | 2.1 |
| 2 | 5.1 | 4.6 | 3.7 | 3.3 | 3.2 | 3.2 |
| 3 | 5.0 | 4.6 | 3.9 | 3.6 | 3.4 | 3.2 |
| 4 | 5.0 | 4.5 | 3.7 | 3.3 | 3.1 | 3.0 |
| 5 | 5.2 | 4.4 | 3.4 | 2.8 | 2.4 | 2.2 |
| 6 | 5.3 | 4.7 | 4.0 | 3.6 | 3.5 | 3.3 |
| 7 | 5.4 | 4.8 | 4.3 | 4.1 | 4.0 | 3.8 |
| 8 | 5.3 | 4.7 | 4.2 | 4.1 | 3.8 | 3.6 |

EXAMPLE 2

Preparation of a Stabilized Live Vaccine Containing an Attenuated Live Varicella Virus as an Active Component Into MRC-5 cell cultures in 20 Roux bottles, each having a culturing area of 210 $cm^2$, is inoculated varicella virus Oka strain seed virus, followed by culturing in substantially the same manner as described in Reference Example 2. After completion of the culturing, the cultured medium is discarded. The infected cells in each Roux bottle are washed twice with 200 ml of PBS (−). Subsequently, 20 ml of 0.05% (w/v) trisodium salt of EDTA is superposed upon the infected cells in each Roux bottle, and the cells are detached, by pipetting, from the inner wall surface of the Roux bottle and suspended in the liquid, to thereby obtain an infected-cell suspension. The infected-cell suspensions in the bottles are pooled together. Then the pooled suspension is centrifuged at 2,000 rpm for 10 minutes at 4° C. to thereby separate the suspension into a supernatant and the cells. The supernatant is discarded to harvest pellets of infected cells. The harvested cells are re-suspended in 100 ml of liquid (A) for suspending virus, which has been prepared in Reference Example 5. Then, the obtained suspension is subjected to one cycle of freeze-thawing and then, to ultrasonication (20 kHz, 150 mA, 0.3 second/ml) in an ice water bath, followed by centrifugation at 1,000 rpm for 10 minutes at 4° C. to thereby separate the suspension into cells and a supernatant. The supernatant containing virus separated from cells is collected.

The collected supernatant is employed as a bulk material of live vaccine. 30 ml of the obtained bulk material of live vaccine is sampled for testing, and the remaining 70 ml of the bulk material of live vaccine is mixed with liquid (A) for suspending vaccine, which has been prepared in Reference Example 5, to thereby prepare 140 ml of a final bulk of live vaccine. 30 ml of the thus prepared final bulk is sampled for testing, and the rest of the bulk is dispensed into vials each having a volume of 3 ml in an amount of 0.5 ml per vial, followed by lyophilization. Then, filling of the vial with nitrogen gas and air-tight sealing of the vial with a rubber stopper are conducted. These vaccine vials are stored at 4° C. In using the lyophilized vaccine stored in the vials, 0.7 ml of distilled water for injection is added to the vaccine to completely dissolve the vaccine, just before the vaccine is used. Thus, the vaccine is provided for use in the form of a solution.

The above-obtained sample of the bulk material of live vaccine, the above-obtained sample of the final bulk of live vaccine, and 20 vaccine vials are subjected to testings for safety, effectiveness and homogeneity for confirming the eligibility as a vaccine. The testings are performed in accordance with the "Lyophilized Attenuated Live Varicella Vaccine" in the Minimum Requirements for Biological Products (1989) provided for in the Notification No. 195 of the Ministry of Health and Welfare, Japan. As a result of the testings, it has been found that the virus content of the above-mentioned vaccine in the vial is $2\times10^4$ PFU/0.5 ml, and that the vaccine passes all of the testings. Consequently, it is concluded that the vaccine has eligibility as a live vaccine. Further, the vaccine is subjected to testing for storage in substantially the same manner as in Example 1. Results of the testing reveal that this vaccine has a stability which is equal to or higher than that attained by liquid 7. Thus, it has been confirmed that the live vaccine is an excellent stabilized live vaccine.

EXAMPLE 3

Testing for Storage of Tetravalent Live Vaccine

Using liquid (B) for suspending virus, which has been obtained in Reference Example 6, a bulk material of live varicella vaccine (V) is prepared in substantially the same manner as described in Example 2.

Separately, each of viruses of measles, rubella and mumps is individually cultured in substantially the same manner as described in Reference Example 3.

With respect to a measles virus, after completion of the culturing, the cultured medium is discarded. The infected cells are washed with PBS (−) to remove $Ca^{2+}$ ions and $Mg^{2+}$ ions. Subsequently, a 1/20 volume of Medium 199 (manufactured and sold by DIFCO, USA), or MEM free of both $Ca^{2+}$ ions and $Mg^{2+}$ ions, is superposed upon the infected cells, and the cells are detached, by pipetting, from the inner wall surface of the culturing vessel and suspended in the liquid, to thereby obtain an infected-cell suspension.

Then, the obtained suspension is subjected to one cycle of freeze-thawing and then, to low-speed centrifugation (at 2,000 rpm for 10 minutes at 4° C.) to thereby separate the suspension into cells and a supernatant. The supernatant containing virus is collected as a measles virus suspension.

With respect to respective viruses of rubella and mumps, after completion of the culturing, the cultured medium containing the virus is subjected to low-speed centrifugation (at 2,000 rpm for 10 minutes at 4° C.) to thereby obtain a supernatant. The supernatant is then concentrated to a 1/20 volume by means of a cellulose membrane (fractionating molecular weight: 300 kilodalton, manufactured and sold by Millipore Corporation, U.S.A). The resultant concentrated medium is then subjected to ultracentrifugation (4° C., 20,000 rpm, 90 minutes for mumps virus, 180 minutes for rubella virus) to separate pellets of virus from a supernatant. The supernatant is discarded and the virus is suspended in Medium 199, or MEM free of both $Ca^{2+}$ ions and $Mg^{2+}$ ions, to obtain a virus suspension with respect to the respective viruses of rubella and mumps.

Each virus suspension obtained above is mixed with an equivolume of liquid (C) for suspending virus, obtained in Reference Example 7, to thereby prepare three types of bulk materials of live vaccines with respect to each of measles, rubella and mumps, as follows:

(1) Bulk materials of live vaccines of measles (M1), rubella (R1) and mumps (MU1) are prepared by adding an equivolume of liquid (C) for suspending virus to respective virus suspensions prepared using Medium 199.

(2) Bulk materials of live vaccines of measles (M2), rubella (R2) and mumps (MU2) are prepared by adding trisodium salt of EDTA to respective virus suspensions prepared using Medium 199 so that the final concentration becomes 0.15% (w/v), and by further adding thereto an equivolume of liquid (C) for suspending virus.

(3) Bulk materials of live vaccines of measles (M3), rubella (R3) and mumps (MU3) are prepared by adding an equivolume of liquid (C) for suspending virus to each virus suspension prepared using MEM free of $Ca^{2+}$ ions and $Mg^{2+}$ ions.

Subsequently, the bulk materials of live vaccines are mixed according to formulations indicated in Table 5 below, to thereby prepare three final bulks of vaccines.

TABLE 5

| | Mixing ratio of live vaccines (ml) | | | |
|---|---|---|---|---|
| Final bulk No. | 500 | 100 | 200 | 200 |
| 1 | V | M1 | R1 | MU1 |
| 2 | V | M2 | R2 | MU2 |
| 3 | V | M3 | R3 | MU3 |

Subsequently, each final bulk of vaccine is dispensed into vials, each having a volume of 3 ml, in an amount of 0.5 ml per vial, in substantially the same manner as described in Example 1. The vaccine in each vial is subjected to lyophilization. After the lyophilization, the vaccine is then subjected to testing for effectiveness of the stabilizer at 37° C. to confirm the stability as a tetravalent vaccine dispensed in a small amount. The effectiveness testing is performed by the plaque assay (for viruses of varicella, measles and rubella) and the $TCID_{50}$ determination (for mumps virus) as described in Reference Examples 10 and 11. Results are shown in Table 6 below. The final bulk No. 3 is most excellent as a stabilized tetravalent live vaccine.

TABLE 6

Results of testing for storage stability of stabilized tetravalent live vaccine

| Final bulk (containing stabilizer) | Titer = log (PFU/ml) or $TCID_{50}$ | | | | | |
|---|---|---|---|---|---|---|
| | Before lyophilization | Days of storing at 37° C. after lyophilization | | | | |
| | | 0 | 7 | 14 | 21 | 28 |
| No. 1 | | | | | | |
| Varicella | 5.0 | 3.6 | 3.0 | 2.7 | 2.2 | 2.1 |
| Measles | 6.1 | 5.6 | 5.2 | 4.9 | 4.9 | 4.8 |
| Rubella | 4.8 | 4.5 | 4.3 | 4.2 | 4.1 | 4.1 |
| Mumps | 6.1 | 5.7 | 5.2 | 4.9 | 4.9 | 4.7 |
| No. 2 | | | | | | |
| Varicella | 5.1 | 4.2 | 3.6 | 3.3 | 3.2 | 3.0 |
| Measles | 6.1 | 5.6 | 5.1 | 5.0 | 4.8 | 4.7 |
| Rubella | 4.8 | 4.5 | 4.4 | 4.2 | 4.2 | 4.1 |
| Mumps | 6.1 | 5.6 | 5.1 | 4.9 | 4.8 | 4.7 |
| No. 3 | | | | | | |
| Varicella | 5.1 | 4.6 | 4.1 | 3.9 | 3.7 | 3.6 |
| Measles | 6.1 | 5.6 | 5.2 | 5.0 | 4.9 | 4.8 |
| Rubella | 4.8 | 4.5 | 4.3 | 4.2 | 4.2 | 4.1 |
| Mumps | 6.1 | 5.7 | 5.2 | 5.0 | 4.8 | 4.6 |

EXAMPLE 4

Testing for Vaccine Stabilizing Effect of Purified Hydrolyzed Gelatin

Liquid (A1) for suspending virus is prepared which has substantially the same composition as that of liquid (A) for suspending virus described in Reference Example 5, except that trisodium salt of EDTA is omitted.

Further, liquid (A2) for suspending virus is prepared which has substantially the same composition as that of liquid (A) for suspending virus described in Reference Example 5, except that purified hydrolyzed gelatin obtained in Reference Example 9 is used instead of the hydrolyzed gelatin and that trisodium salt of EDTA is omitted. Using liquids (A), (A1) and (A2) for suspending virus individually, a lyophilized live varicella vaccine is prepared in substantially the same manner as described in Example 2. Each of the obtained live vaccines is subjected to testing for storage stability at 37° C. Test results are shown in Table 7 below. It is found that liquid (A2) for suspending virus has a virus stabilizing effect equal to that of liquid (A). That is, it has been confirmed that when purified hydrolyzed gelatin free of $Ca^{2+}$ ions and $Mg^{2+}$ ions is used as one of the stabilizer components, trisodium salt of EDTA is not necessary.

TABLE 7

Varicella vaccine stabilizing effect of purified hydrolized gelatin (Testing for effectiveness of Stabilizer)

| Stabilizer | Titer = log (PFU/ml) | | | | | |
|---|---|---|---|---|---|---|
| Liquid for suspending virus | Before lyophilization | Days of storing at 37° C. after lyophilization | | | | |
| | | 0 | 7 | 14 | 21 | 28 |
| A | 5.4 | 4.9 | 4.5 | 4.3 | 4.2 | 3.9 |
| A1 | 5.1 | 4.6 | 3.9 | 3.6 | 3.3 | 3.1 |
| A2 | 5.3 | 4.9 | 4.4 | 4.1 | 4.0 | 3.8 |

EXAMPLE 5

Preparation of a Stabilized Live Vaccine Containing an Attenuated Recombinant Varicella Virus as an Active Component Substantially the same procedure as in Example 2 is repeated except that attenuated recombinant varicella virus rVH17-5 Oka strain [ECACC (European Collection of Animal Cell Cultures) Accession Number V92041523] which has been prepared by ligating a hepatitis B virus gene to the genomic DNA of attenuated varicella virus Oka strain, is employed as a seed virus, to thereby prepare a recombinant varicella virus vaccine. The thus obtained vaccine is subjected to the same testings for safety, effectiveness, homogeneity and storage as in Example 2. As a result, it has been found that the vaccine has eligibility as a live vaccine and has excellent stability. Thus, it has been confirmed that the live vaccine is an excellent stabilized live vaccine which is comparable to the vaccine obtained in Example 2.

What is claimed is:

1. A stabilized live vaccine comprising a virus component comprised of at least one varicella virus selected from the group consisting of an attenuated live varicella virus and an attenuated live recombinant varicella virus, and a stabilizer comprising (a) from 0.5 to 10% (w/v) of sucrose or a mixture of from 0.5 to 10% (w/v) of lactose, from 0.2 to 6.0% (w/v) of sorbitol and from 0.02 to 1.0% (w/v) of cysteine; (b) from 0.01 to 5.0% (w/v) of sodium glutamate; (c) from 0.02 to 1.0% (w/v) of gelatin; and (d) from 0.5 to 10% (w/v) of hydrolyzed gelatin, in terms of the concentration in the stabilized live vaccine, said gelatin and said hydrolyzed gelatin being free of $Ca^{2+}$ ions and $Mg^{2+}$ ions to the extent that $Ca^{2+}$ ions and $Mg^{2+}$ ions are not detected by a calorimetric titration method using a chelating reagent, wherein said gelatin and said hydrolyzed gelatin, each being substantially free of $Ca^{2+}$ ions and $Mg^{2+}$ ions, are respectively obtained by subjecting gelatin and a hydrolyzed gelatin, each containing at least one of $Ca^{2+}$ ions and $Mg^{2+}$ ions, to at least one treatment selected from the group consisting of dialysis treatment, gel filtration treatment, cation exchange resin treatment, chelating resin treatment, and a masking treatment with a chelating reagent, to thereby remove said at least one of $Ca^{2+}$ ions and $Mg^{2+}$ ions.

2. The stabilized live vaccine according to claim 1, wherein said virus component further comprises at least one additional attenuated live virus selected from the group consisting of attenuated live viruses of measles, rubella and mumps.

3. The stabilized live vaccine according to claim 2, wherein said at least one additional attenuated live virus is a mixture of attenuated live viruses of measles, rubella and mumps.

4. A method for stabilizing a live vaccine, which comprises adding a stabilizer to a live vaccine comprising a virus component wherein said virus component comprises at least one varicella virus selected from the group consisting of an attenuated live varicella virus and an attenuated recombinant varicella virus, wherein said stabilizer comprises (a) from 0.5 to 10% (w/v) of sucrose or a mixture of from 0.5 to 10% (w/v) of lactose, from 0.2 to 6.0% (w/v) of sorbitol and from 0.02 to 1.0% (w/v) of cysteine;

(b) from 0.01 to 5.0% (w/v) of sodium glutamate;

(c) from 0.02 to 1.0% (w/v) of gelatin; and (d) from 0.5 to 10% (w/v) of hydrolyzed gelatin, wherein percentage is determined in terms of the concentration in the resultant mixture of said live vaccine and said stabilizer, said gelatin and said hydrolyzed gelatin being free of $Ca^{2+}$ ions and $Mg^{2+}$ ions to the extent that $Ca^{2+}$ ions and $Mg^{2+}$ ions are not detected by the calorimetric titration method using a chelating reagent, wherein said gelatin and said hydrolyzed gelatin, each being free of $Ca^{2+}$ ions and $Mg^{2+}$ ions, are respectively obtained by subjecting gelatin and a hydrolyzed gelatin, each containing at least one of $Ca^{2+}$ ions and $Mg^{2+}$ ions, to at least one treatment selected from the group consisting of dialysis treatment, gel filtration treatment, cation exchange resin treatment, chelating resin treatment, and a masking treatment with a chelating reagent, to thereby remove said at least one of $Ca^{2+}$ ions and $Mg^{2+}$ ions.

5. The method according to claim 4, wherein said virus component further comprises at least one additional attenuated live virus selected from the group consisting of attenuated live viruses of measles, rubella and mumps.

6. The method according to claim 5, wherein said at least one additional attenuated live virus is a mixture of attenuated live viruses of measles, rubella and mumps.

7. The method according to claim 4, wherein said mixture of said live vaccine and said stabilizer is in the form of a liquid product or a lyophilized product.

8. A stabilized live vaccine comprising a virus component comprised of at least one varicella virus selected from the group consisting of an attenuated live varicella virus and an attenuated live recombinant varicella virus, and a stabilizer comprising:

(a) from 0.5 to 10% (w/v) of sucrose or a mixture of from 0.5 to 10% (w/v) of lactose, from 0.2 to 6.0% (w/v) of sorbitol, from 0.02 to 1.0% (w/v) of cysteine; (b) from 0.01 to 5.0% (w/v) of sodium glutamate; (c) from 0.02 to 1.0% (w/v) of gelatin; and (d) from 0.5 to 10% (w/v) of hydrolyzed gelatin, in terms of the concentration in the stabilized live vaccine, said gelatin and said hydrolyzed gelatin being free of $Ca^{2+}$ ions and $Mg^{2+}$ ions to the extent that $Ca^{2+}$ ions and $Mg^{2+}$ ions are not detected by a calorimetric titration method using a chelating reagent.

9. The stabilized live vaccine according to claim 8, wherein said virus component further comprises at least one additional attenuated live virus selected from the group consisting of attenuated live viruses of measles, rubella and mumps.

10. The stabilized live vaccine according to claim 9, wherein said at least one additional attenuated live virus is a mixture of attentuated live viruses of measles, rubella and mumps.

* * * * *